United States Patent
Morou-Bermudez

(10) Patent No.: US 11,340,174 B1
(45) Date of Patent: May 24, 2022

(54) SCREENING TEST FOR CARIES ACTIVITY AND CARIES RISK ASSESSMBASED ON THE COMBINED PRODUCTION OF ACID AND ALKALI IN THE ORAL CAVITY (ACID-BASE CARIES TEST: ABC-TEST)

(71) Applicant: Evangelia Morou-Bermudez, San Juan, PR (US)

(72) Inventor: Evangelia Morou-Bermudez, San Juan, PR (US)

(73) Assignee: University of Puerto Rico, San Juan, PR (US)

(*) Notice: Subject to any disclaimer, the term of this patent is extended or adjusted under 35 U.S.C. 154(b) by 0 days.

(21) Appl. No.: 15/431,743

(22) Filed: Feb. 13, 2017

Related U.S. Application Data

(60) Provisional application No. 62/293,883, filed on Feb. 11, 2016.

(51) Int. Cl.
*G01N 21/80* (2006.01)
*G01N 33/48* (2006.01)
*G01N 33/52* (2006.01)

(52) U.S. Cl.
CPC ............ *G01N 21/80* (2013.01); *G01N 33/48* (2013.01); *G01N 33/52* (2013.01); *G01N 2800/18* (2013.01)

(58) Field of Classification Search
CPC .... G01N 21/80; G01N 2800/18; G01N 33/48; G01N 33/52; Y10T 436/144444; Y10T 436/17; Y10T 436/171538
USPC .... 436/63, 95, 106, 108, 163, 164; 422/400, 422/430
See application file for complete search history.

(56) References Cited

U.S. PATENT DOCUMENTS

| | | | | |
|---|---|---|---|---|
| 4,359,455 | A * | 11/1982 | Nakamura | G01N 33/52 424/49 |
| 6,152,887 | A * | 11/2000 | Blume | A61B 10/0045 600/573 |
| 7,160,731 | B2 * | 1/2007 | Takagi | G01N 33/84 436/162 |
| 2003/0113266 | A1 * | 6/2003 | Matsumoto | A61K 8/60 424/9.71 |
| 2004/0228762 | A1 * | 11/2004 | Matsumoto | A61K 6/0058 422/400 |

OTHER PUBLICATIONS

Shu et al. Oral Microbiology Immunology, vol. 22, 2007, pp. 61-66.*
Morou-Bermudez et al. JDR Clinical & Translational Research, vol. 2, issue 2, Oct. 10, 2016, pp. 132-141.*
Toro et al. Archives of Oral Biology, vol. 55, 2010, pp. 249-254.*
Morou-Bermudez et al. Puerto Rico Health Sciences Journal (PRHSJ), vol. 30, No. 4, Dec. 2011, pp. 165-166.*

* cited by examiner

*Primary Examiner* — Maureen Wallenhorst
(74) *Attorney, Agent, or Firm* — Hoglund & Pamias, PSC; Roberto J Rios

(57) ABSTRACT

Effective monitoring of the acid/base physiology of dental plaque is considered in caries risk assessment. The invention provides a methodology for caries risk assessment and a kit of biochemical tests for acid/alkali generation in dental plaque and in saliva as a screening instrument for identifying subjects with caries. The invention provides simple chair-side tests that measure the ability of dental plaque and/or saliva to metabolize sugars concomitantly with the ability to metabolize urea and other salivary nitrogenous substrates.

12 Claims, 3 Drawing Sheets

SCREENING TEST FOR CARIES ACTIVITY AND CARIES RISK ASSESSMBASED ON THE COMBINED PRODUCTION OF ACID AND ALKALI IN THE ORAL CAVITY (ACID-BASE CARIES TEST: ABC-TEST)

GOVERNMENT INTEREST

The claimed invention was made with U.S. Government support under grant number: R21 DE021135 awarded by The National Institutes of Health (NIH). The government has certain rights in this invention.

BACKGROUND OF THE INVENTION

Reducing or eliminating disparities in the distribution and severity of dental caries requires targeted interventions that can be widely adopted by the community and by oral health professionals. For such interventions to be implemented, it is necessary to develop validated, low-cost, rapid screening tools that can be used to identify individuals at risk. Currently, there are several biochemical and bacteriological tests available for assessing the acid-generating potential of plaque and saliva in a chair-side manner. These tests require long incubation periods (48 hours) and their diagnostic and predictive value has not been yet established. In addition, a number of comprehensive models have been developed for assessing and predicting caries risk. Consistent with the multifactorial etiology of dental caries these models include multiple clinical, psychosocial and biological risk factors. Many of these factors are either difficult to assess with the available instruments or require a dental examination that limits their use to dentists. Despite significant advancements in our understanding of the biological processes associated with caries onset and progression, there is no validated caries screening instrument that is suitable for use by the lay pubic or by health professionals.

Therefore, there is a need to identify and address novel risk factors to develop a low-cost, rapid screening tool that can be used to identify the risk factors in caries risk screening.

SUMMARY OF THE INVENTION

This invention illustrates a new approach for caries screening and caries risk assessment.

The invention is based on the ability to generate acids from sugars and the ability to generate alkali from endogenous sources in the dental plaque and in the saliva. These are the risk factors most closely related to caries onset and progression.

According to an aspect of the invention, a simple, rapid method to measure these opposing activities together is provided to enhance the accuracy of a screening instrument for determining caries risk.

Among the various sources of alkali in the oral cavity, urea is the most abundant. Urease activity appears to be linked to sugar consumption and to levels of mutants streptococci.

According to one aspect of the invention, alkali generation from urea and acid production from sugars in plaque are closely related risk factors and are evaluated concomitantly to assess caries risk more accurately.

According to another aspect of the invention, the present invention provides an array of simple, rapid, colorimetric tests to rapidly and concomitantly assess the ability of dental plaque and saliva to generate alkali from urea and other endogenous sources, as well as acid from sugars.

According to an objective of this invention, the validity and reliability of these tests to identify individuals with untreated caries was determined, in order to develop a unique, multidimensional test to predict dental caries, particularly in high-risk children.

BRIEF DESCRIPTION OF THE DRAWINGS

Further features and advantages of the invention will become apparent from the following detailed description taken in conjunction with the accompanying figures showing illustrative embodiments of the invention, in which.

DETAILED DESCRIPTION OF THE INVENTION

Figure 3:
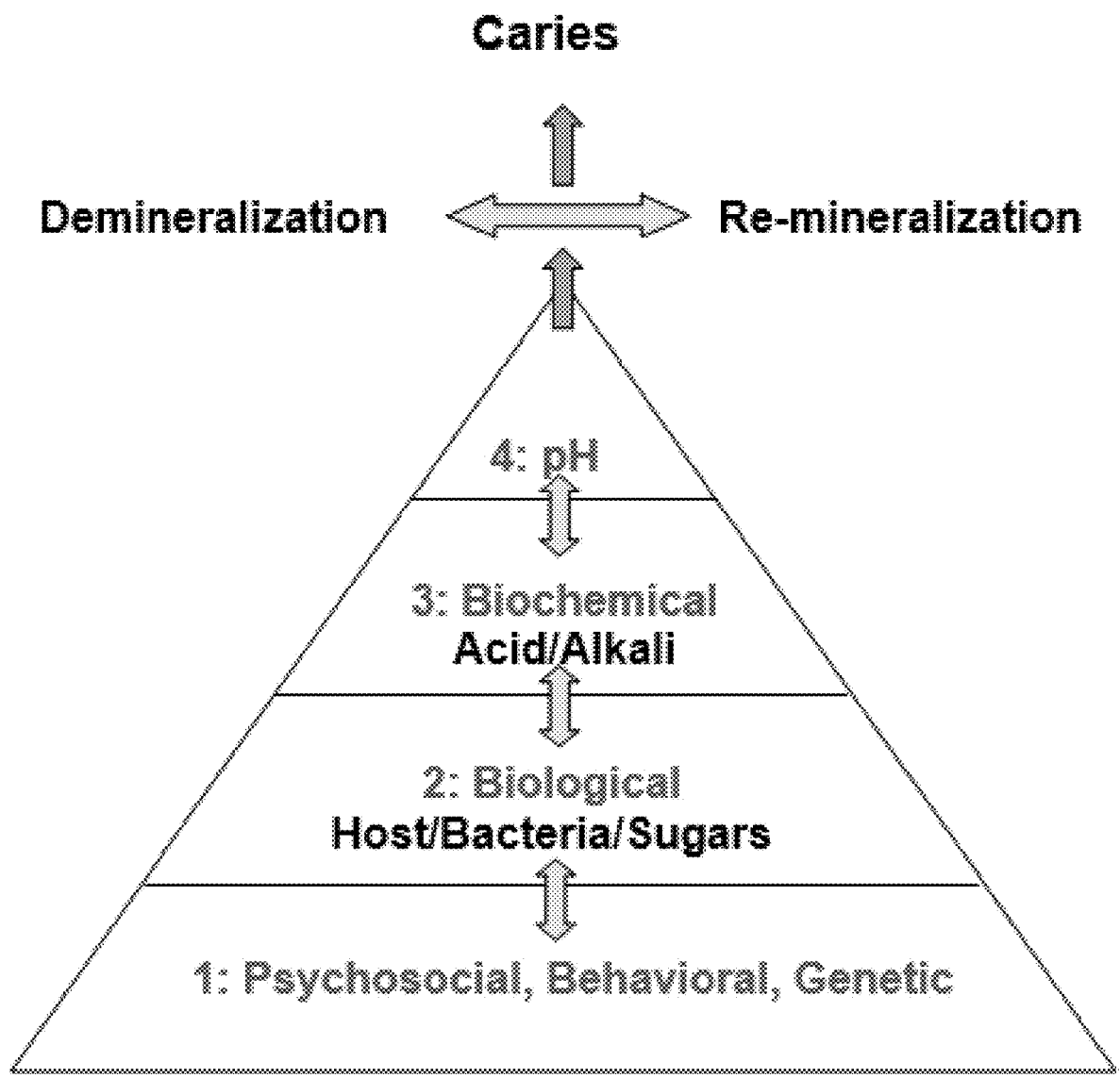
FIG. 3 illustrates a Caries Risk Pyramid (CRP), according to the present invention.

The present invention proposes a novel approach founded on the concept named Caries Risk Pyramid-CRP (FIG. 3). The CRP model states that the etiological factors leading to the onset of dental caries, as well as the complex interactions among them can be sequentially organized according to the level in which their influence is exerted, forming a pyramid. The tip of this pyramid (Level 4) consists of a single factor, the plaque pH, which ultimately controls the chemical phenomena that lead to caries formation (de-mineralization/re-mineralization). The pH of the plaque is determined by biochemical pathways that generate acid and alkali in the plaque, as well as by other potential buffering systems (Level 3). The expression and activity of these systems depends on biological factors, which include host-related factors (saliva, immune system), oral ecology and sugar availability (Level 2). The base of the pyramid (Level 1) consists of the multiple psychosocial, behavioral and genetic factors that determine the biological profile of an individual. According to this model the ability to generate acids from sugars and the ability to generate alkali from urea, or other endogenous sources in the dental plaque and/or in the saliva appear to be two closely related factors, which summarize the combined effect of all other caries risk factors and are closely related to disease development. Therefore, the present invention measures these abilities together in a simple, rapid way providing an accurate screening instrument for dental caries, and possibly for predicting future caries risk.

Materials and Methods

Study Design and Population.

The invention is based on a cross-sectional study on a convenience sample of 185 adult, healthy subjects (21-61 years-old). The sample size was estimated using preliminary data from a previous clinical study to detect significant differences in plaque urease activity between clinically caries-free subjects and subjects with at least one untreated caries lesion, with a level of significance at 0.05 and 80% power. Participants were recruited using flyers within the University of Puerto Rico Medical Sciences Campus (UPR-MSC). Inclusion requirement was the presence of at least one anterior and one posterior tooth in each quadrant of the mouth. Exclusion criteria included medical conditions requiring pre-medication for routine dental treatment; bleeding of the gums; treatment with antibiotics within previous 2 months; medications affecting salivary flow; hyposalivation; immunosuppression; orthodontic or prosthetic appliances; smoking; hormonal disturbances, pregnancy, and breastfeeding. Eligible participants provided written informed consent approved by the IRB of the UPR-MSC (Protocol #A0060111).

Clinical Procedures

Participants were instructed to refrain from oral hygiene procedures for 24 hours prior to the appointment and to eat or drink nothing but water since the night before. On the day of the study visit the participants answered a brief sociodemographic questionnaire and provided a 24-hour diet recall, which was used to quantify sugar consumption. The participants rinsed their mouth with water for 30 seconds immediately prior to sample collection. Approximately 3 mls of whole unstimulated saliva were collected. Subsequently, the teeth of each quadrant were rinsed for 5 seconds with water spay, isolated with cotton rolls, and dried for 5 sec with air spray. Supragingival plaque was collected from the buccal surfaces of one molar and one incisor tooth in each quadrant and pooled into a pre-weighted micro-centrifuge tube. All sample collections took place in the morning hours, between 7 am and 10 am. Saliva and plaque samples were kept on ice and transferred to the adjacent laboratory within less than one hour from collection. Following the collection of plaque and saliva samples the dental assistant brushed the participant's teeth prior to the dental examination.

Dental exams were performed using the International Caries Detection and Assessment System (ICDAS) criteria. One calibrated examiner performed all exams. A training and calibration exercise was conducted in the beginning of the study on 30 subjects with a total of 4,703 tooth surfaces. The inter-rater reliability (% Agreement and weighed kappa±SE) as calculated on the last five patients of the training/calibration exercise (785 surfaces) was 97.94% and 0.72±0.03 (P<0.001). Intra-rater reliability was evaluated periodically during the study on 10% of the subjects; intra-rater kappa was 0.62 (98.39% agreement). Four digital bitewing radiographs were taken in the radiology clinic of the UPR School of Dental Medicine, unless the participant could provide recent (within 1 to two years, depending on the clinical caries status of the participant) bitewings of good diagnostic value from his/her dentist. The bitewings were used for diagnostic as well as research purposes. All x-rays were evaluated by the same examiner using the ICDAS criteria for x-rays (*ICDAS foundation*, 2015). When a disagreement existed between the clinical exam and the x-rays on an interproximal surface, the x-ray score predominated. For all other dental surfaces, the clinical score predominated over the x-ray score.

For the purposes of the invention, subjects were classified as "caries-active" (CA) if they had at least one un-treated caries lesion with dentinal involvement (clinical ICDAS score ≥4 and/or x-ray ICDAS score ≥3) (*ICDAS foundation*, 2015); this definition included recurrent lesions under existing or missing restorations. All other subjects, including those with ICDAS 1-3 lesions (lesions restricted to the enamel), those with restorations with no clinical or radiographic evidence of recurrent decay, and teeth extracted due to caries were classified as "caries-inactive" (CI).

To assess the reliability of the tests, a second plaque and saliva sample was collected 1 to 4 weeks after the first visit using the same methodology.

Biochemical and Microbiological Procedures

The ability of dental plaque and saliva to generate alkali and acid production from sugars was measured with custom made colorimetric tests. These tests consist of solutions containing a pH indicator and buffer at neutral baseline pH, as well as a variety of substrates of interest. Tests PU (Plaque Urea) and SU (Saliva Urea) measured pH changes from the metabolism of 10 mM urea in plaque and in saliva, respectively; PG (Plaque Glucose) and SG (Saliva Glucose) tests measured pH changes from the metabolism of 10 mM glucose in plaque (PG) or saliva (SG); tests PUG (Plaque Urea Glucose) and SUG (Saliva Urea Glucose) measured pH changes from the simultaneous metabolism of 10 mM urea and 10 mM glucose in plaque (PUG), or in saliva (SUG). In order to consider all other possible alkali generating substrates available in the saliva of each participant we used the SPG (Saliva Plaque Glucose) test. This test was similar to the PG test, but it also included clarified saliva from the same patient. Control solutions with a) no sample and b) no substrate were included to determine background pH changes.

The tests were performed immediately following the collection of plaque and saliva samples. The amount of plaque used for the PU, PG, PUG, and SPG tests was standardized by wet weight (0.1 mg); the amount of saliva for the SU, SG, and SUG test was standardized by volume (50 µl). The plates were covered with sealing tape and incubated at 37° C. Test results were recorded after 1 hour, 2 hours, 3 hours and overnight. The score for each test at each time point corresponded to the pH reading of the test minus the pH change of the control solution. The pH was determined in 0.25 unit increments using a colorimetric pH scale (Phenol Red). All tests were performed and scored by one calibrated technician, who was blind to the caries status of the subjects. The correlation (Spearman Rho) between the visual color scale measurements and a calibrated pH meter (SympHony B20, VWR, Radnor Pa.) was 0.92 (P<0.001), as determined by a pilot calibration experiment.

A commercial bacteriological test for salivary mutants streptococci and lactobacilli (CRT-bacteria, Ivoclar Vivadent, Liechtenstein) was included for comparison against the biochemical tests. The CRT tests were performed with 1 ml saliva each according to the manufacturer's instructions. Their results were read after 48 and 96 hours and they were expressed as a categorical variable with scores between 1 ($\leq 10^5$ CFU/ml) and 4 ($>10^5$ CFU/ml) according to the manufacturer's instructions.

Analytical Procedures

Summary statistics were used to describe the study group. The Chi-squared distribution and Mann-Whitney tests were used to compare CA and CI groups according to demographic and clinical characteristics. Non-parametric ROCs were initially calculated for each test at each time point. The 3 hr results for the biochemical tests and the 96 hours scores for the bacteriological tests had the best score distribution and the best ROCs, compared to the other time-points, and were therefore selected for the further analysis. The validity of each test was assessed using sensitivity, specificity, positive and negative predictive values (PPV and NPV), and roc regression adjusted for age and gender. The scores of each biochemical test (which corresponded to the adjusted pH values at each time point) were inverted for this analysis, as higher pH values indicate lower risk. In order to determine which combination of tests best explains the caries status, multivariate analysis was performed using logistic regression models. The diagnostic value of these multivariate models was assessed with the Stata commands "lroc" and "estat classification". The likelihood ratio (LR) test was used to assess interactions and to compare different multivariate logistic regression models for the classification of CA and CI subjects. The reliability of each test between the two visits was evaluated using weighted kappa statistics. Data were analyzed using the STATA version 12.0 software.

Results

The study group consisted of 81 males and 104 females aged between 21 and 61 years of age (mean 33.6±10.6 years). 81 subjects (43.78%) were considered "caries-active" (CA) according to the study criteria, while 104 subjects (56.22%) were "caries-inactive" (CI) as shown in Table 1 below.

Figure 1:
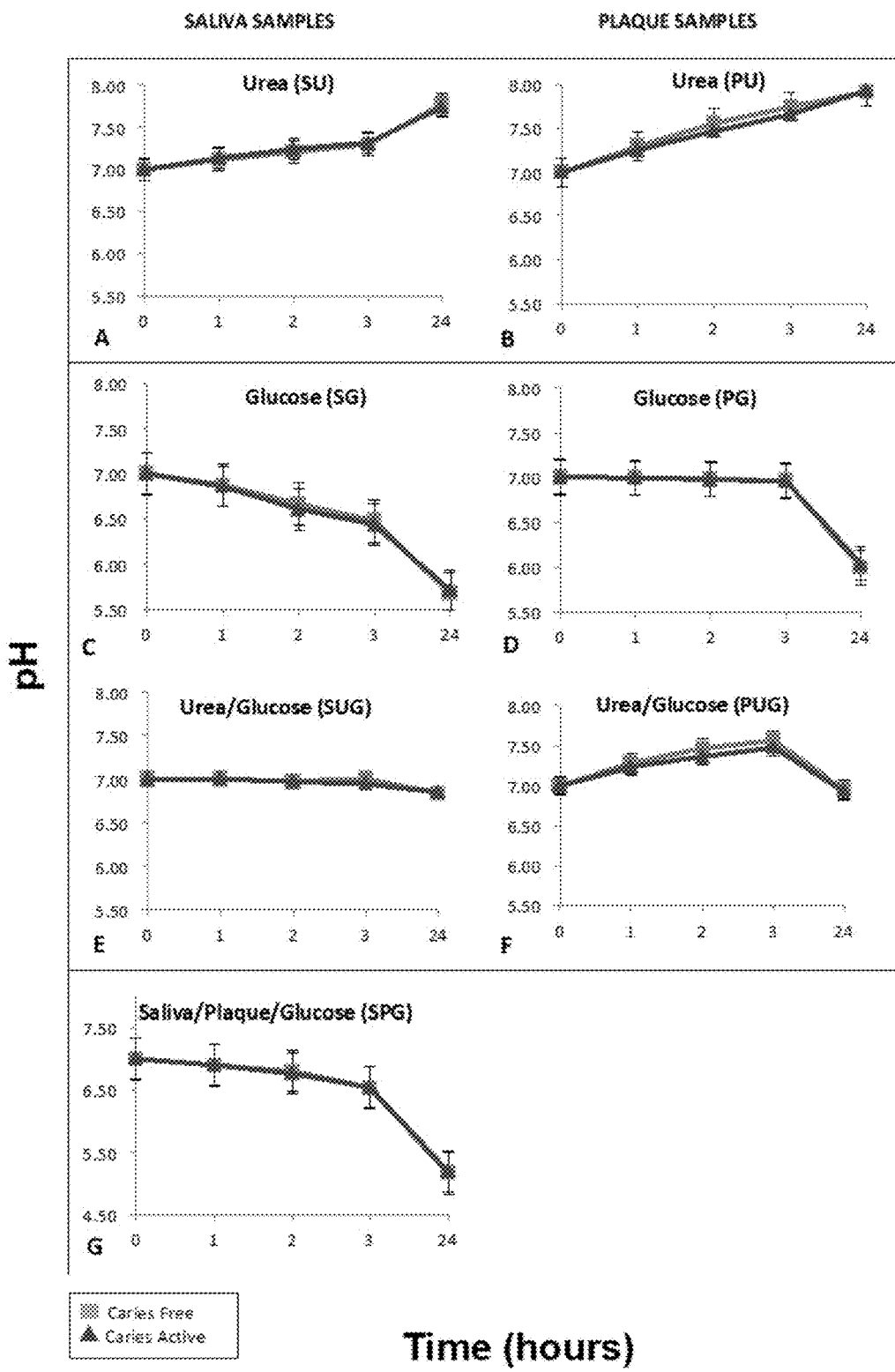
FIGS. 1A-1G show plots of observed pattern of pH changes in the biochemical tests over time in the CA and CI groups, according to the present invention.

In the plaque samples, the metabolism of urea produced on average a 0.7 unit increase in the pH within the first three hours (FIG. 1, plot B), while the metabolism of an equal molar amount of glucose had very small effect on the pH within the first three hours (on average 0.05 pH units) (FIG. 1, plot D). Consequently, when both substrates were available to the plaque samples at the same time, there was an initial increase in the pH (about 0.5 pH units in the first three hours) and the final pH after overnight incubation returned to neutral levels (FIG. 1, plot F). In the saliva samples the metabolism of urea produced on average a 0.32 unit increase in the pH in the first three hours (FIG. 1, plot A), while the metabolism of equal molar glucose produced on average a

TABLE 1

|  | Caries Inactive (n = 104) % or Mean ± SD (Median) | Caries Active (n = 81) | P Value |
|---|---|---|---|
| Gender |  | 56.2% males | 43.8% males |
| Age | 33.6 ± 10.8 (30) y | 33.6 ± (31) y | >0.05$^b$ |
| Education | 62.8% college | 37.2% college | 0.005$^a$ |
| Dental insurance | 63.4% private | 36.6% private | 0.035$^a$ |
| Frequency of dental visits | 78% every 6 months | 65% every 6 months | 0.060$^a$ |
| Frequency of brushing | 90% more than twice a day | 83% more than twice a day | >0.05$^a$ |
| Sugar consumption | 3.9 ± 2.4 (3.75) | 3.8 ± 2.1 (4) | >0.05$^b$ |
| Amount of plaque | 8.9 ± 4.2 (8) mg | 9.7 ± 3.9 (9.5) mg | 0.083$^b$ |
| Saliva CFU | 90.1 ± 72.9 (74) | 101.3 ± 102.5 (87) | >0.05$^b$ |
| Salivary mutants (CRT score) | 1.75 ± 0.86 (2) | 2.14 ± 1.00 (2) | 0.008$^b$ |
| Salivary lactobacilli (CRT score) | 1.53 ± 0.62 (1) | 1.91 ± 0.90 (2) | 0.005$^b$ |
| Enamel, noncavitated (ICDAS 1 and 2) | 6.5 ± 5.1 (5) | 7.5 ± 6.8 (5) | >0.05$^b$ |
| Enamel, cavitated (ICDAS 3) | 1.1 ± 1.6 (0) | 1.4 ± 1.5 (1) | 0.025$^b$ |
| Dentine (ICDAS 4 to 6) | 0 | 2.6 ± 2.6 (2) |  |
| Total restorations | 14.4 ± 11 (13) | 14.2 ± 12.4 (13) | >0.05$^b$ |
| DFS | 9.96 ± 8.64 (9) | 13.4 ± 11.05 (12) | 0.027$^b$ |

There were no significant age and gender differences between the two groups (P>0.05). The CA group had significantly fewer subjects with college level education (P=0.005) and fewer subjects with private dental insurance (P=0.035). CA subjects had significantly higher numbers of cavitated lesions restricted to the enamel (ICDAS score 3) compared to CI subjects (P=0.025), but there was no significant difference in the numbers of non-cavitated "white-spot" lesions (ICDAS scores 1 and 2), or in the numbers of existing restorations between the CA and CI subjects. CA subjects had significantly higher salivary loads of mutants streptococci and lactobacilli compared to caries-inactive subjects (P<0.01). No significant differences were observed between the CA and CI subjects with respect to the amount of plaque, sugar consumption, and total bacterial load in the saliva (P>0.05).

0.5 unit drop in the pH during the same period (FIG. 1, plot C). When both substrates were available simultaneously to the saliva samples, no change was observed in the pH during the first three hours, and only a very small pH drop (on average 0.17 units) was observed after the overnight incubation (FIG. 1, plot E). The pattern of the SPG test was more similar to that of the SG test, rather than the PG test (FIG. 1, plot G). The trend of the PUG test over time was significantly different between CI and CA subjects (P=0.015). No differences were observed in the trends of the PU, PG, SU, SG or SUG tests between the two groups.

The sensitivity of the biochemical tests ranged between 14.8% (PG) and 89.8% (SUG), and the specificity between 18.9% (SPG) and 84.6% (PG), as shown in Table 2 below.

TABLE 2

| Test | Sensitivity (95% CI) | Specificity (95% CI) | Positive Predictive Value (95% CI) | Negative Predictive Value (95% CI) | Sensitivity + Specificity | ROC (95% CI), Adj. Age, Gender P Value Compared with CRT-LB | | Kappa (% Agreement between Visits) |
|---|---|---|---|---|---|---|---|---|
| PU$^a$ | 34.1(25.4, 42.8) | 68.6(60.1, 77.1) | 40.5(31.5, 49.6) | 62.3(53.4, 71.2) | 102.7 | 0.58(0.50, 0.66) | >0.05 | 0.40(88.4) |
| PG$^a$ | 14.8(9.7, 19.9) | 84.6(79.4, 89.8) | 42.9(35.7, 50.0) | 56.1(48.9, 63.2) | 99.4 | 0.50(0.41, 0.58) | 0.023 | 0.26(94.6) |

TABLE 2-continued

| Test | Sensitivity (95% CI) | Specificity (95% CI) | Positive Predictive Value (95% CI) | Negative Predictive Value (95% CI) | Sensitivity + Specificity | ROC (95% CI), Adj. Age, Gender P Value Compared with CRT-LB | | Kappa (% Agreement between Visits) |
|---|---|---|---|---|---|---|---|---|
| PUG[a] | 87.0(78.8, 95.1) | 40.5(28.5, 52.4) | 44.4(32.4, 56.5) | 85.0(76.3, 93.7) | 127.5 | 0.59(0.51, 0.67) | >0.05 | 0.44(92.0) |
| SPG[a] | 75.0(66.0, 84.0) | 18.9(10.7, 27.0) | 38.6(28.5, 48.7) | 52.6(42.3, 63.0) | 93.9 | 0.48(0.40, 0.56) | 0.009 | 0.23(93.5) |
| SU | 57.1(47.8, 66.5) | 58.6(49.3, 68.0) | 53.9(44.4, 63.3) | 61.8(52.6, 71.0) | 115.7 | 0.51(0.43, 0.60) | 0.035 | 0.44(95.5) |
| SU[a] | 68.8(58.5, 79.0) | 21.7(12.6, 30.9) | 37.9(27.2, 48.7) | 50.0(38.9, 61.1) | 90.5 | 0.49(0.40, 0.57) | 0.030 | |
| SG[a] | 56.8(46.0, 67.6) | 29.6(19.6, 39.5) | 40.4(29.7, 51.1) | 44.8(34.0, 55.7) | 86.4 | 0.49(0.41, 0.57) | 0.005 | 0.46(96.1) |
| SUG[a] | 89.6(84.9, 94.8) | 27.1(19.8, 34.3) | 46.1(38.0, 54.2) | 79.3(73.0, 85.9) | 116.9 | 0.60(0.53, 0.68) | >0.05 | 0.40(94.9) |
| CRT-MS | 51.9(43.6, 60.1) | 57.0(48.8, 65.2) | 43.1(34.9, 51.3) | 65.3(57.5, 73.2) | 108.9 | 0.61(0.53, 0.69) | >0.05 | 0.65(92.3) |
| CRT-LB | 50.0(42.2, 57.8) | 57.3(49.6, 65.0) | 43.1(35.3, 50.8) | 64.0(56.5, 71.4) | 107.3 | 0.63(0.55, 0.71) | | 0.65(95.3) |

The bacteriological tests had a sensitivity of 50.0 to 51.9% and specificity around 57.0%. The test with the highest sum of sensitivity plus specificity was the PUG test (127.5%) and the lowest was the SG test (86.4%). The PPVs were between 38.6% (SPG) and 53.9% (SU), and NPVs ranged between 44.8% (PU) and 85.0% (PUG).

Figure 2:
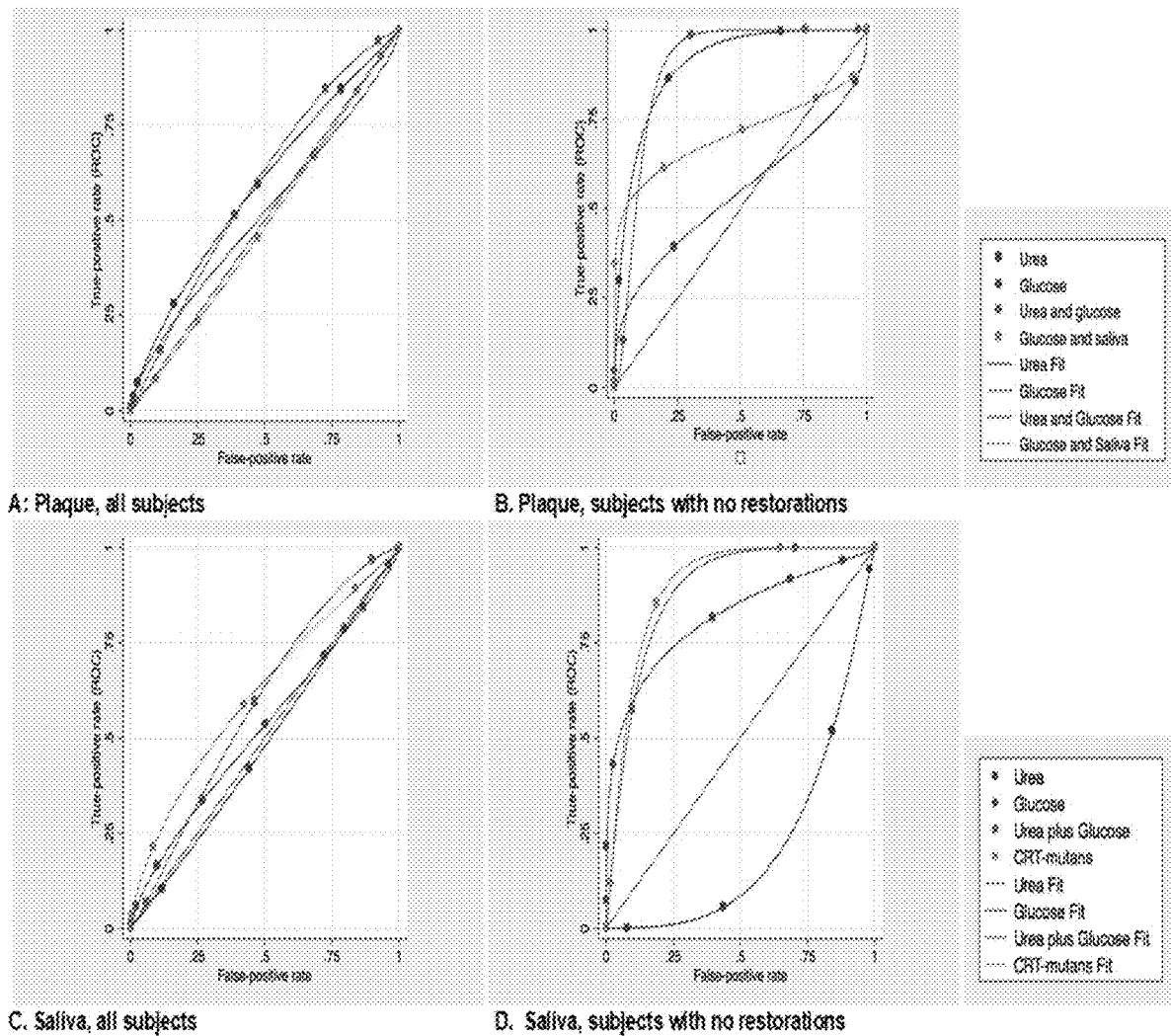
FIGS. 2A-2D show shows plots of age and gender adjusted ROCs of the biochemical and bacteriological tests for identification purposes, according to the present invention.

The largest AUC was the one of the CRT-*lactobacillus* test (0.63, 95% CI 0.55, 0.71). The AUCs of the CRT-mutants, PU, PUG and SUG tests were between 0.58 to 0.61 and they did not differ significantly from the CRT-*lactobacillus* (P>0.05) (FIG. 2 plots A-C; Table 2), while the remaining tests (PG, SU, SPG, and SG) were significantly lower compared to the CRT-*lactobacillus* test (P<0.05). The ROC of the SU test was inversed relative to the ROCs of the other biochemical tests.

The ROCs of the study tests, with the exception of the PG and the CRT-*lactobacillus*, were larger in 17 subjects who did not have existing restorations (AUC 0.78 to 0.90, FIG. 2, plots B-D). These subjects (10 CI, 7 CA) did not differ significantly from the rest of the group with respect to age, gender, sugar consumption, amount of plaque, total bacterial load in saliva, or numbers of mutants streptococci in saliva (P>0.05). The ROCs of the PG and CRT-*lactobacillus* test were significantly smaller than the CRT-mutants test (P<0.05) in these subjects.

Test scores that were significantly associated with caries status were the following: PUG scores 8.0 and above (adjOR: 0.20, 95% CI 0.05, 0.76); SUG score 7.25 and above (adjOR 0.23, 95% CI 0.08, 0.69), SPG score 6.5 (adjOR: 3.09, 95% CI 1.23, 7.59), CRT-mutants score >2 (adjOR: 2.86, 95% CI 1.32, 6.20), and CRT-*lactobacillus* score >2 (adjOR: 4.81, 95% CI 1.82, 12.75). Based on these data each subject was assigned one "Biochemical Risk" point for each of the following situations: PUG<8.0, SUG<7.25, SPG=6.5 and one "Bacteriological Risk" point for each of the bacteriological tests (CRT-mutants and CRT-*lactobacillus*) with score of 3 and above. The sum of biochemical and biological risk points for each participant was defined as "Biological Risk". The ""Biochemical Risk" model had significantly better diagnostic values than the "Bacteriological qRisk" (LR test P<0.001) as shown in Table 3 below.

TABLE 3

| Model | Variables | Caries Threshold | Se | Sp | PPV | NPV | CC | Se + Sp | AUC |
|---|---|---|---|---|---|---|---|---|---|
| M1: Biochemical | "Biochemical Risk"[a] | ICDAS 4 | 37.0 | 81.7 | 61.2 | 62.5 | 62.16 | 118.7 | 0.660 |
| | | ICDAS 3 | 90.2 | 32.1 | 76.8 | 56.7 | 73.51 | 122.3 | 0.682 |
| M2: Bacteriological | "Bacteriological Risk"[b] | ICDAS 4 | 38.3 | 76.9 | 56.4 | 61.5 | 60.00 | 115.2 | 0.576 |
| M3: Biological | M1 + M2 | ICDAS 3 | 100.0 | 0.0 | 71.4 | NC[c] | 71.35 | 100.0 | 0.523 |
| | | ICDAS 4 | 32.1 | 99.0 | 96.3 | 65.2 | 69.73 | 131.1 | 0.745 |
| | | ICDAS 3 | 92.4 | 26.4 | 75.8 | 58.3 | 73.61 | 118.8 | 0.673 |
| M4: Psychosocial | Age, gender, education, insurance, frequency of dental visits | ICDAS 4 | 50.0 | 85.7 | 72.0 | 70.0 | 70.59 | 135.7 | 0.695 |
| M5: | M3 + M4 | ICDAS 3 | 95.8 | 19.6 | 73.6 | 66.7 | 72.94 | 115.4 | 0.680 |
| | | ICDAS 4 | 70.83 | 89.80 | 83.61 | 80.73 | 81.76 | 160.6 | 0.846 |
| Comprehensive | | ICDAS 3 | 90.8 | 41.2 | 78.3 | 65.6 | 75.88 | 132.0 | 0.753 |

The "Biological Risk" had significantly better diagnostic value compared to the "biochemical" and the "bacteriological" risks (P<0.001), but it was not significantly better than a model composed of simple psychosocial factors, including age, gender, education, insurance and frequency of dental visits (P>0.05). When the "Biological Risk" was included into the psychosocial model, the resulting model had an ROC of 0.847, a combined sensitivity/specificity of 160.2, and it would correctly classify about 82% of the subjects according to their true caries status. This model was significantly better compared to the psychosocial (LR test P<0.001) and to the one with only Biological Risk (LR test: P=0.011). Addition of any further tests, such as the PU, SU, SG, and PG tests, or other biological and psychosocial variables did not significantly improve the diagnostic values of the model.

The reliability of the PU, PUG, SU, SUG and SG tests between the two visits was average, with weighed kappas ranging between 0.40 (PU, SUG) to 0.46 (SG) (Table 2). The reliability of the PG and SPG test was poor (kappa: 0.26, 0.23, respectively). The results of the bacteriological tests were more consistent between the two visits (kappa: 0.65).

Discussion

This invention presents a novel approach for assessing caries risk based on emerging evidence, which strongly suggests that effective monitoring of the acid: base physiology of dental plaque must be considered in caries risk assessment. Our caries screening instruments incorporate a new risk factor that has never been considered in caries risk assessment, specifically, the ability of bacteria in dental plaque and saliva to generate alkali from urea and other endogenous nitrogen sources. According to the Caries Risk Pyramid Model this activity should be evaluated together with the process of acid production in order to assess caries risk more effectively.

Alkali and acid production in plaque and in saliva was measured, both individually and together, with a simple colorimetric method. The rationale for selecting urea as the alkali generating substrate is because urea is more abundant in the oral cavity compared to other nitrogenous substrates. Furthermore, oral ureolysis is the only source of alkali in the oral cavity whose relationship with caries development has been examined longitudinally. Each mole of urea produces two moles of ammonia, while each mole of glucose produces two moles of pyruvate, respectively. The amount of sample was standardized and appropriate controls for background pH were included. In the plaque samples the production of alkali from urea predominated over the production of acid from an equal molar amount of glucose during the first three hours, while in the saliva, the two activities were equivalent. This is in agreement with previous clinical studies, which have shown that the urease activity in plaque is higher than that of saliva. The PG test did not show significant acid production from glucose during the first three hours, however, the SPG test that had the same amount of plaque and glucose but it also included the supernatant from the subject's saliva showed more pronounced acid production. Other investigators have also observed that glucose utilization and acid production in oral bacteria is much greater with saliva present. The ROC of the SU test was inverted compared to the rest of the tests, indicating that in the original scoring scale of the test, higher pH values corresponded to higher risk. This is in agreement with our previous longitudinal study in children, which demonstrated that although in plaque urease activity was negatively associated with caries risk, in saliva high urease activity was associated with increased caries risk and increased levels of mutants streptococci. Overall, these findings demonstrate that the custom-made tests used in this study represented reasonably accurately the biochemical processes of oral ureolysis and glycolysis. This simple technology can be easily adapted into a much faster, reliable and very low-cost chair-side instrument for professional or personal use.

The ROCs of the urea containing tests (PU, PUG, and SUG) were statistically similar to those of the bacteriological tests. However, the PUG and SUG tests, which contain both urea and glucose, had the highest sum of sensitivity and specificity. Furthermore, the combination of PUG, SUG and SPG tests had significantly larger ROC than the combination of the two bacteriological tests. This finding provides support for our hypothesis that measuring acid and alkali production in plaque together could be a more accurate indicator of caries risk than measuring each of these abilities individually. The SU test behaved similarly to the bacteriological tests instead of the biochemical tests, in other words, higher pH values, or higher urease activity in saliva corresponded to higher risk. This finding is consistent with the findings of our previous study as explained previously. The PG, SG, and SPG tests, which measure acid production from glucose, had significantly smaller ROCs; their diagnostic values were somewhat lower compared to those reported for similar sugar-containing colorimetric tests in pre-school children. The SPG test, had poor diagnostic values, but it was significant both in the univariate, and the multivariate regression models. Overall, the ROCs obtained in this study were small, but this is not surprising because biological tests are generally reported to have poor diagnostic value in adults and in older children (older than 6 years). Bacteriological caries activity tests appear to be more accurate in preschool children. It has also been proposed that the diagnostic value of biological caries risk tests depends largely on the caries experience of the test population. In our invention, however, both the biochemical and bacteriological tests could be a lot more accurate in subjects who did not have existing restorations, irrespectively of the age, and even if these subjects had lost teeth in the past due to caries. Interestingly, the CRT-*lactobacillus* test was significantly less accurate than the CRT-mutants test in these subjects. Our results were not different when secondary caries were excluded from the analysis (data not shown). Albeit based on a very small number of subjects, these observations suggest that the presence of "iatrogenic risk factors", (i.e. dental restorations), may impact the diagnostic value of biological caries test. Larger studies will be necessary to evaluate the impact of age, overall caries experience and presence of dental restorations on the diagnostic quality of biological caries tests.

In order for a caries risk test to be considered acceptable for clinical use, a combined sensitivity plus specificity of 160% is generally required. Since no single biological test has been demonstrated to comply with these requirements, efforts have been made to incorporate these tests in multivariate models that include a variety of psychosocial and clinical caries risk factors. Evidence for the validity of these models in caries risk assessment is weak and the comparisons are almost impossible because of the different populations, designs, and disease definitions utilized in each study. It is generally recognized that the risk factor with the highest predictive value in caries risk assessment models is the previous dental experience, but the extent to which the incorporation of biological tests can increase the diagnostic or predictive value of such models is under debate. In our study, the multivariate model that was consisted only of biological tests (biochemical and bacteriological) was not significantly different than the one that consisted exclusively of psychosocial risk factors (age, gender, education, health insurance and frequency of dental visits). However, the model that included both the biological and the psychosocial factors had significantly better diagnostic value compared to the biological and the psychosocial models individually. Notably, our model was validated in adults of a wide age range and various levels of previous dental experience. Still, the model could classify with clinically acceptable accuracy individuals with even one, non-cavitated carious lesion in the dentine without using any clinical information. This makes it suitable for use by other health care professionals, lay public and potentially parents or care givers in a home use protocol.

In conclusion, the invention proposes that measuring the ability of dental plaque and saliva to metabolize urea and other salivary nitrogenous substrates together with the ability to generate acid from sugars using simple chair-side tests can be a promising approach for identifying subjects with untreated caries, particularly when no dental restorations are present. Further longitudinal studies are planned to validate these tests in children and infants with no previous exposure to the oral health care system, as screening tools for Early Childhood Caries (ECC). Ultimately, these simple tests have substantial potential as a predictor of future caries risk, either independently, or in combination with other caries risk factors.

The invention claimed is:

1. A method for screening and assessing a risk of caries in a subject, said method comprising:
    obtaining from said subject an amount of a plaque sample;
    mixing said plaque sample with a solution containing: an alkali-generating substrate, an acid-generating substrate and a pH indicator;
    incubating the solution at a predetermined temperature and for a predetermined time;
    comparing a color of said solution against a colorimetric pH scale; and
    assessing a caries risk in said subject by matching said color of the solution mixed with said plaque sample with a color on the colorimetric pH scale that correlates with a known caries risk level, wherein a high caries risk is determined when the color matched on the colorimetric pH scale corresponds to a pH level below a predetermined pH value of 8.0 for the solution mixed with said plaque sample, said predetermined pH value is established based on at least one of: a concentration of plaque in the solution or a duration time of incubation.

2. The method of claim 1, wherein said alkali-generating substrate comprises urea.

3. The method of claim 1, wherein said alkali-generating substrate comprises a nitrogenous substrate.

4. The method of claim 1, wherein said acid-generating substrate comprises glucose.

5. The method of claim 1, wherein the amount of said plaque sample is standardized by one of: wet weight and volume.

6. The method of claim 1, wherein said predetermined temperature is 37° C. and said predetermined time is between 30 min to 3 hours.

7. A method for screening and assessing a risk of caries in a subject, said method comprising:
    obtaining from said subject an amount of a saliva sample;
    mixing said saliva sample with a solution containing: an alkali-generating substrate, an acid-generating substrate and a pH indicator;
    incubating the solution at a predetermined temperature and for a predetermined time;
    comparing a color of said solution against a colorimetric pH scale; and
    assessing a caries risk in said subject by matching said color of the solution mixed with said saliva sample with a color on the colorimetric pH scale that correlates with a known caries risk level, wherein a high caries risk is determined when the color matched on the colorimetric pH scale corresponds to a pH level below a predetermined pH value of 7.25 for the solution mixed with said saliva sample, said predetermined pH value is established based on at least one of: a concentration of saliva in the solution or a duration time of incubation.

8. The method of claim 7, wherein said alkali-generating substrate comprises urea.

9. The method of claim 7, wherein said alkali-generating substrate comprises a nitrogenous substrate.

10. The method of claim 7, wherein said acid-generating substrate comprises glucose.

11. The method of claim 7, wherein the amount of said saliva sample is standardized by one of: wet weight and volume.

12. The method of claim 7, wherein said predetermined temperature is 37° C. and said predetermined time is between 30 min to 3 hours.

* * * * *